(12) United States Patent
Tuulari et al.

(10) Patent No.: US 10,736,574 B2
(45) Date of Patent: Aug. 11, 2020

(54) PERFORMANCE MONITORING SYSTEM

(71) Applicant: POLAR ELECTRO OY, Kempele (FI)

(72) Inventors: Esa Tuulari, Kempele (FI); Jukka Happonen, Oulunsalo (FI); Daniela Olstad, Oslo (NO)

(73) Assignee: POLAR ELECTRO OY, Kempele (FI)

( * ) Notice: Subject to any disclaimer, the term of this patent is extended or adjusted under 35 U.S.C. 154(b) by 315 days.

(21) Appl. No.: 15/863,412

(22) Filed: Jan. 5, 2018

(65) Prior Publication Data
US 2018/0235547 A1 Aug. 23, 2018

(30) Foreign Application Priority Data

Feb. 21, 2017 (EP) ..................................... 17157124

(51) Int. Cl.
*A61B 5/11* (2006.01)
*A61B 5/00* (2006.01)
(Continued)

(52) U.S. Cl.
CPC .......... *A61B 5/6895* (2013.01); *A61B 5/0004* (2013.01); *A61B 5/0205* (2013.01);
(Continued)

(58) Field of Classification Search
CPC ......... A61B 5/02; A61B 5/024; A61B 5/0205; A61B 5/11; A61B 5/1118; A61B 5/1123; A61B 5/1124; A61B 5/224; A61B 5/6887; A61B 5/6895; A61B 2503/10; A61B 5/7278; A61B 5/0004; A61B 5/7405; A61B 5/742; A61B 5/7455; A63C 11/22; A63C 11/222; A63C 11/225; A63C 2203/18;
(Continued)

(56) References Cited

U.S. PATENT DOCUMENTS

2007/0082789 A1 4/2007 Nissila et al.
2010/0292050 A1* 11/2010 DiBenedetto ...... A63B 71/0686
482/9

(Continued)

FOREIGN PATENT DOCUMENTS

EP 1 908 499 A1 4/2008
EP 3 000 396 A1 3/2016
(Continued)

OTHER PUBLICATIONS

European Search Report for corresponding Application No. EP 17 15 7124, 2 pages, dated Aug. 11, 2017.
(Continued)

*Primary Examiner* — Christian Jang
(74) *Attorney, Agent, or Firm* — FisherBroyles, LLP

(57) ABSTRACT

A system for monitoring performance of a user includes at least one processor, and at least one memory including a computer program code. The at least one memory and the computer program code are configured, with the at least one processor, to cause the system to perform operations including obtaining force data measured by at least one force sensor coupled with one or more poles and velocity data measured by at least one sensor for measuring velocity of the user, determining poling power based on the force data and the velocity data, and outputting a poling power indicator based on the determined poling power.

18 Claims, 9 Drawing Sheets

(51) Int. Cl.
- *A63C 11/22* (2006.01)
- *A61B 5/0205* (2006.01)
- *G06F 19/00* (2018.01)
- *G09B 19/00* (2006.01)
- *A61B 5/22* (2006.01)
- *A63B 69/18* (2006.01)
- *A61B 5/024* (2006.01)
- *G06K 9/00* (2006.01)

(52) U.S. Cl.
CPC .............. *A61B 5/11* (2013.01); *A61B 5/1123* (2013.01); *A61B 5/224* (2013.01); *A61B 5/7278* (2013.01); *A61B 5/742* (2013.01); *A61B 5/7405* (2013.01); *A61B 5/7455* (2013.01); *A63C 11/222* (2013.01); *A63C 11/225* (2013.01); *G06F 19/3481* (2013.01); *G09B 19/0038* (2013.01); *A61B 5/024* (2013.01); *A61B 5/1118* (2013.01); *A61B 2503/10* (2013.01); *A63B 69/18* (2013.01); *A63B 2220/51* (2013.01); *A63B 2225/52* (2013.01); *A63B 2230/06* (2013.01); *A63C 2203/18* (2013.01); *A63C 2203/22* (2013.01); *A63C 2203/24* (2013.01); *G06K 9/00342* (2013.01)

(58) Field of Classification Search
CPC . A63C 2203/22; A63C 2203/24; A63B 69/18; A63B 2220/51; A63B 2230/06; A63B 2225/52; G06F 19/3481; G06K 9/00342; G09B 19/0038

USPC ........................................................ 600/481
See application file for complete search history.

(56) References Cited

U.S. PATENT DOCUMENTS

2012/0095356 A1* 4/2012 Oleson ............... A63B 24/0062
                                                              600/508
2017/0211997 A1* 7/2017 Kulach ................... G01L 3/247

FOREIGN PATENT DOCUMENTS

| JP | 06246030 A * | 9/1994 |
| WO | 03/002218 A1 | 1/2003 |
| WO | 2016/030768 A3 | 3/2016 |
| WO | 2016/141947 A1 | 9/2016 |
| WO | 2017/139897 A1 | 8/2017 |

OTHER PUBLICATIONS

Myklebust et al., "Morphological Analysis of Acceleration Signals in Cross-Country Skiing," Information extraction and technique transitions detection, 9 pages, Jul. 19, 2010.

Communication pursuant to Rule 114(2) EPC received for EP Patent Application Serial No. 17157124.3 dated Mar. 12, 2020, 4 pages.

* cited by examiner

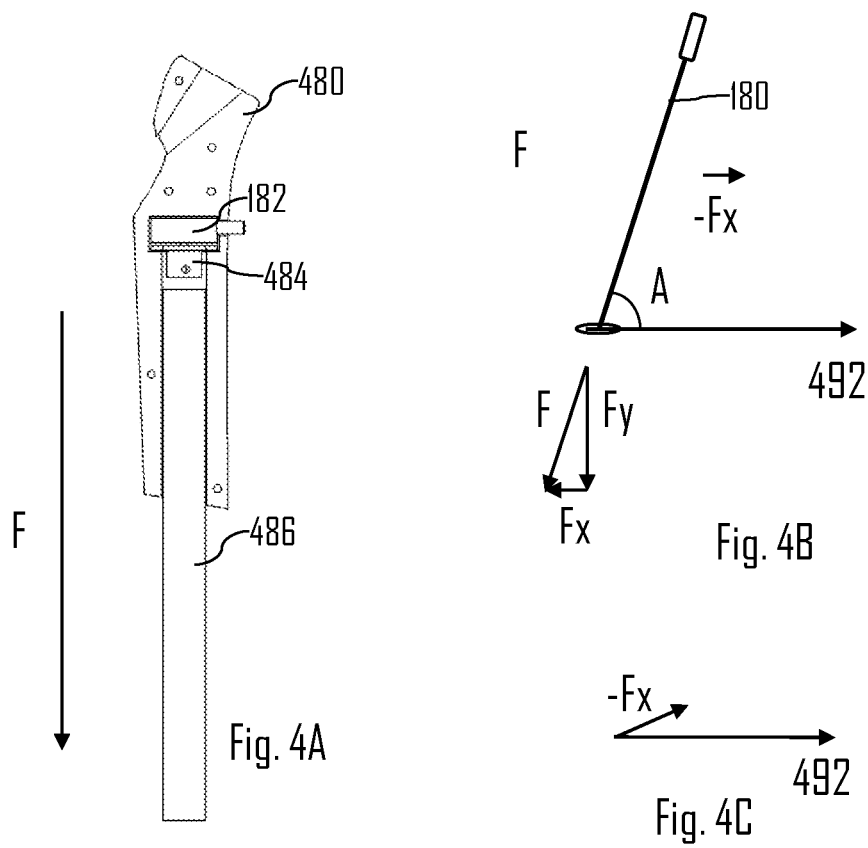
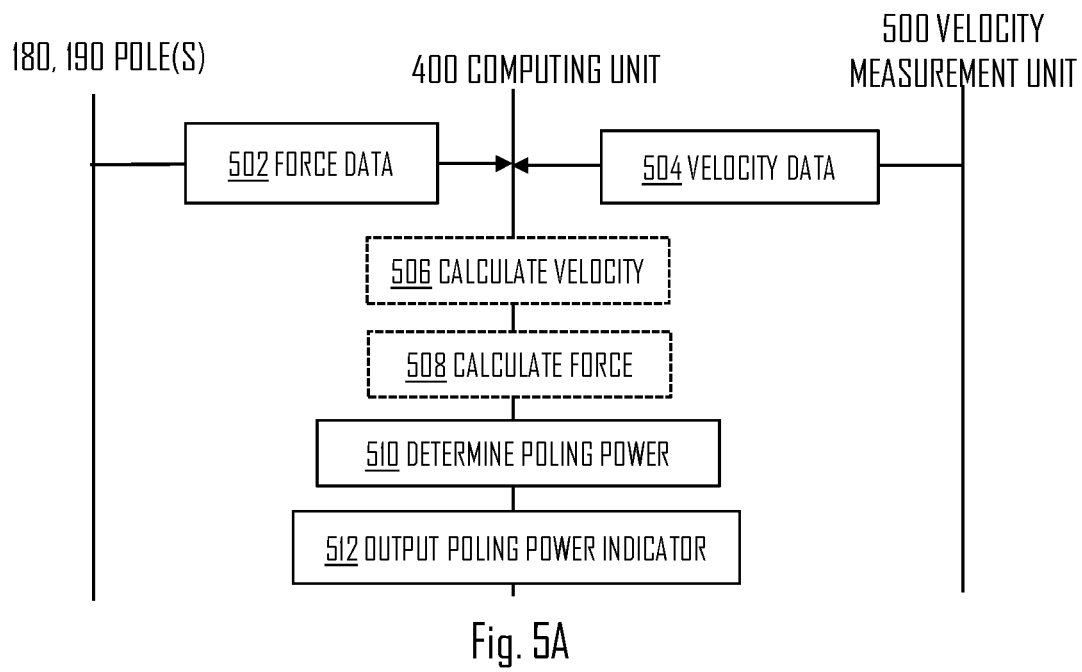
Fig. 5A

PERFORMANCE MONITORING SYSTEM

CROSS-REFERENCE TO RELATED APPLICATION

This application claims benefit to European Application No. 17157124.3, filed Feb. 21, 2017, which is incorporated by reference herein in its entirety.

BACKGROUND

Field

The present invention relates to monitoring performance of a user. More particularly, the present invention relates to systems for measuring and outputting one or more performance metrics of a user or users, such as skier or skiers.

Description of the Related Art

Physical activity monitoring has become topic that increasingly draws attention. There seems to be discussion to provide more and more specific solutions for different sport activities, such as skiing (e.g. nordic skiing, downhill/alpine skiing and telemark skiing) and other activities requiring use of poles. However, it seems that the solutions do not capture some essential parts of physical activity performance monitoring. Therefore, there seems to be room for providing specific performance metric monitoring solutions for activities utilizing poles, such as skiing.

SUMMARY

According to an aspect, there is provided the subject matter of the independent claim. Some embodiments are defined in the dependent claims.

One or more examples of implementations are set forth in more detail in the accompanying drawings and the description below. Other features will be apparent from the description and drawings, and from the claims.

BRIEF DESCRIPTION OF THE DRAWINGS

In the following some embodiments with reference to the attached drawings, in which

FIGS. 4A to 4C illustrate some embodiments;

FIGS. 5A, 5B, 6A, 6B, 7A, 7B illustrate signal diagrams according to some embodiments;

DETAILED DESCRIPTION

The following embodiments are exemplifying. Although the specification may refer to "an", "one", or "some" embodiment(s) in several locations of the text, this does not necessarily mean that each reference is made to the same embodiment(s), or that a particular feature only applies to a single embodiment. Single features of different embodiments may also be combined to provide other embodiments. Furthermore, words "comprising" and "including" should be understood as not limiting the described embodiments to consist of only those features that have been mentioned and such embodiments may contain also features/structures that have not been specifically mentioned.

Figure 1:
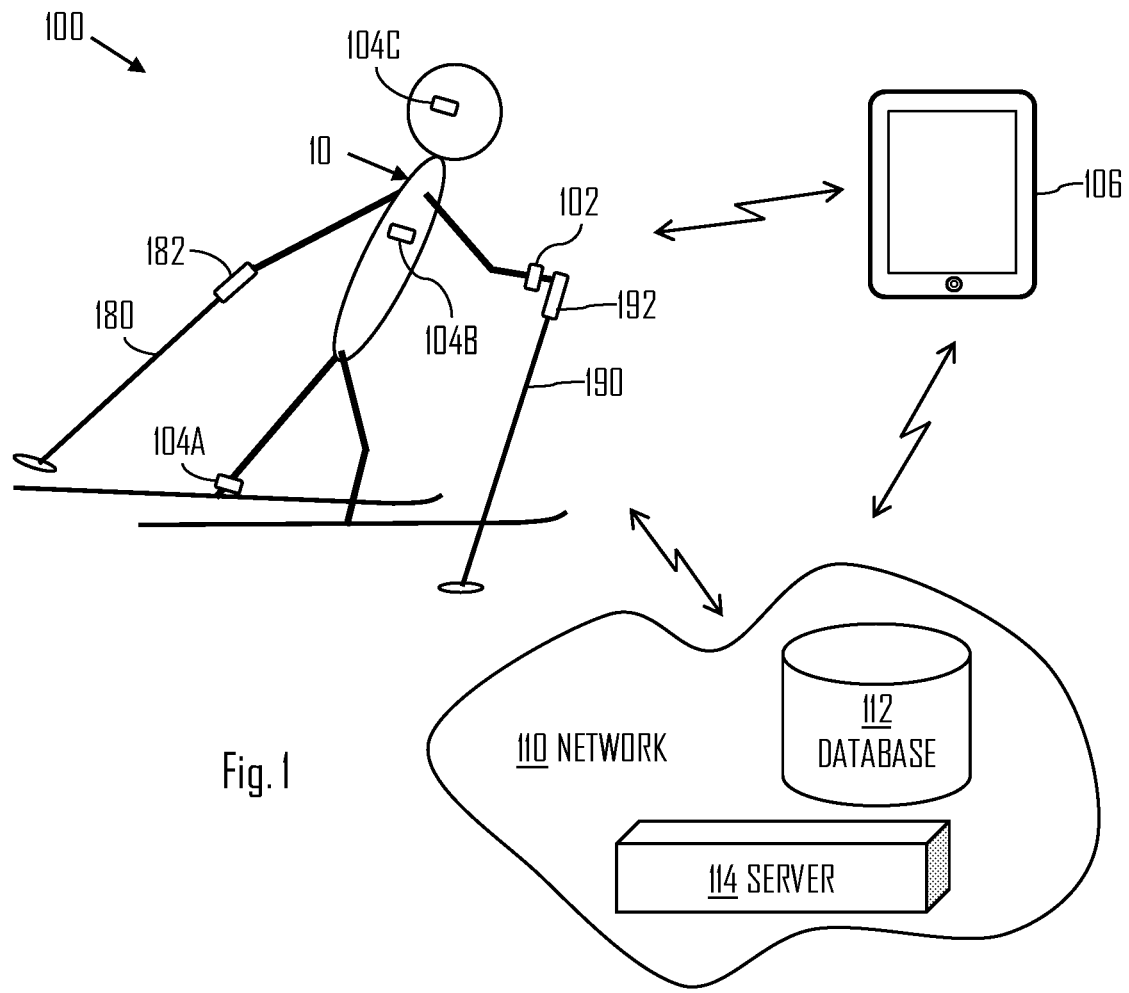
FIG. 1 illustrates a system for measuring performance of a user.

FIG. 1 illustrates an example system to which the embodiments of the invention may be applied. Said system may be a system 100 for monitoring performance of a user 10. For example, performance of skiing or nordic walking may be monitored. Hence, said system may be for monitoring skiing performance, i.e. skiing performance of one or more users 10 (i.e. skiers) may be monitored. However, the monitoring system may be suitable for any activity that utilizes poles similar to poles used during skiing or nordic walking.

Referring to FIG. 1, a user 10 or a skier 10 may be shown. The performance of the user 10 may be monitored (e.g. measured and outputted) utilizing one or more sensor units or devices 102, 104A, 104B, 104C, 182, 192, 106, 112, 114.

Figure 2:
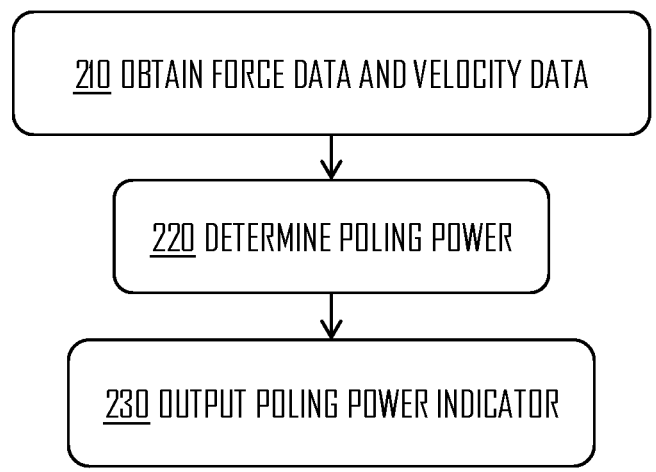
FIG. 2 illustrates a flow diagram according to an embodiment.

FIG. 2 illustrates a flow diagram according to an embodiment. Referring to FIG. 2, the system 100 is configured to perform operations comprising: obtaining force data measured by at least one force sensor 182, 192 coupled with one or more skiing poles 180, 190 and velocity data measured by at least one sensor for measuring velocity of the user (block 210), determining poling power based on the force data and the velocity data (block 220), and outputting a poling power indicator based on the determined poling power (block 230).

In order to perform the operations of blocks 210, 220, 230, the system 100 may comprise at least one at least one processor, and at least one memory including a computer program code, wherein the at least one memory and the computer program code are configured, with the at least one processor, to cause the system 100 to perform operations comprising the operations of blocks 210, 220, 230. For example, the at least one processor and the at least one memory may be comprised in a computing unit of the system. The computing unit may be comprised in a wrist unit 102, in a portable electronic device 104, in the one or more skiing poles 180, 190, and/or in the server 114. In some embodiments, the computing unit is shared between one or more of the described entities.

Referring again to FIG. 1, according to an embodiment, the system 100 may comprise the at least one force sensor 182, 192. The at least one force sensor 182, 192 may be coupled with the one or more poles 180, 190. In an embodiment, the one or more poles 180, 190 are part of the system 100.

Accordingly, in an embodiment, the at least one force sensor 182, 192 comprises a first force sensor 182 coupled with a first skiing pole 180 and a second force sensor 192 coupled with a second skiing pole 190. Such arrangement may enable measuring force associated with each pole 180, 190 used during skiing. As it is known, normally two poles are used during skiing. However, in some embodiments, it may suffice that force associated with one of the poles is measured. For example, it may be determined or assumed that force associated with the poles is substantially the same and thus only one needs to be measured. However, it is sometimes beneficial to independently measure force associated with the first pole and force associated with the second pole.

Still referring to FIG. 1, the system 100 may further comprise the at least one sensor for measuring velocity or speed of the user 10 or is configured to obtain data from said at least one sensor. The velocity data may be used together with the force data to determine the poling power. The poling power may be one metric or indicator of the skiing performance by the user or users.

Said at least one sensor for measuring velocity may be realized by various ways. For example, motion sensor(s) may be used to measure the velocity. In another example, satellite positioning circuitry or circuitries may be used to measure the velocity data. Said at least one sensor may thus comprise, for example, accelerometer(s) (e.g. 3D accelerometer), gyroscope(s) (3D gyroscope), magnetometer(s), and/or satellite positioning circuitry (e.g. a global navigation satellite system (GNSS) circuitry, such as a Global Positioning System (GPS), a GLObal NAvigation Satellite System (GLONASS), and/or Galileo).

The system 100 may further comprise or obtain data from a wrist unit 102 and/or one or more external sensor devices 104A, 104B, 104C. For example, said at least one sensor for measuring velocity may be comprised in the wrist unit 102 and/or in the one or more external sensor devices 104A-C. In some embodiments, the wrist unit 102 and/or the one or more external sensor devices 104A-C comprise additional or different sensors. However, said at least one sensor for measuring the velocity of the user 10 may alternatively or additionally be comprised in the one or more poles 180, 190. Hence, the wrist unit 102 and/or the external sensor device(s) 104A-C and/or their data is not necessarily required.

In addition to the motion sensor(s), satellite positioning circuitry or circuitries and/or the at least one force sensor 182, 192 or data from said sensor(s), the system 100 may comprise or obtain data from further sensor devices. Said further sensor devices may be comprised in the wrist unit 102, in the external sensor device(s) 104A-C and/or in the one or more poles 180, 190. Use of said further sensor devices does not necessarily require use of the described motion sensor(s), satellite positioning circuitry and/or the at least one force sensor 182, 192.

Said further sensor devices may comprise a cardiac activity circuitry for measuring cardiac activity of the user. The cardiac activity circuitry may be configured to be placed at least partially against a body tissue of the user and to measure cardiac activity data of the user. The cardiac activity circuitry may comprise one or more optical sensors, one or more bioimpedance sensors, and/or one or more electrodes (e.g. ECG measurement). Sensor fusion may, in some embodiments, be applied to the cardiac activity circuitry. That is, data from two or more sensors may be used in order to determine cardiac activity of the user. Cardiac activity data may comprise, for example, heart rate of the user, heart rate zone(s) of the user, Heart Beat Interval (HBI) of the user and/or Heart Rate Variability (HRV) of the user. The bioimpedance sensor(s) may be configured to measure cardiac activity of the user. Also, the bioimpedance sensor(s) may configured to, for example, measure skin conductivity and/or skin temperature of the user.

Said further sensor devices may comprise an altitude sensor, such as a barometer, for measuring altitude. Instead or in addition to the barometer, satellite positioning data acquired using the satellite positioning circuitry may be used to determine the altitude.

Referring to FIG. 1, various placements options for the external sensor device(s) 104A-C are given. These may include wrist, arm, leg, ankle, head, ear and chest. However, the placement options are not restricted to these examples.

It is further noted that the elements of the system 100 may be further configured to receive and/or transmit data. For example, the computing unit described above for performing the operations of blocks 210, 220, 230 may further comprise a communication circuitry enabling such data transfer. For example, if the at least one force sensor 182, 192 and the computing unit are comprised in different entities, data transfer may be required.

The system 100 may comprise a portable electronic device 106 (e.g. tablet computer, laptop, mobile phone) for displaying measurement data to the user 10. For example, the power indicator and/or other performance may be displayed on the portable electronic device 106.

The system 100 may comprise a network 110 comprising a database(s) 112 and a server(s) 114. The network 110 may be in communication with the portable electronic device 106, the wrist unit 102, the external sensor device(s) 104A-C, and/or with sensor unit(s) of the poles 180, 190. Said sensor unit(s) of the poles 180, 190 may comprise the at least one force sensor 182, 192 and/or other sensor(s) comprised in the poles, such as said at least one sensor for measuring the velocity, for example. For example, measurement data may be stored in the database 112.

Figure 3:
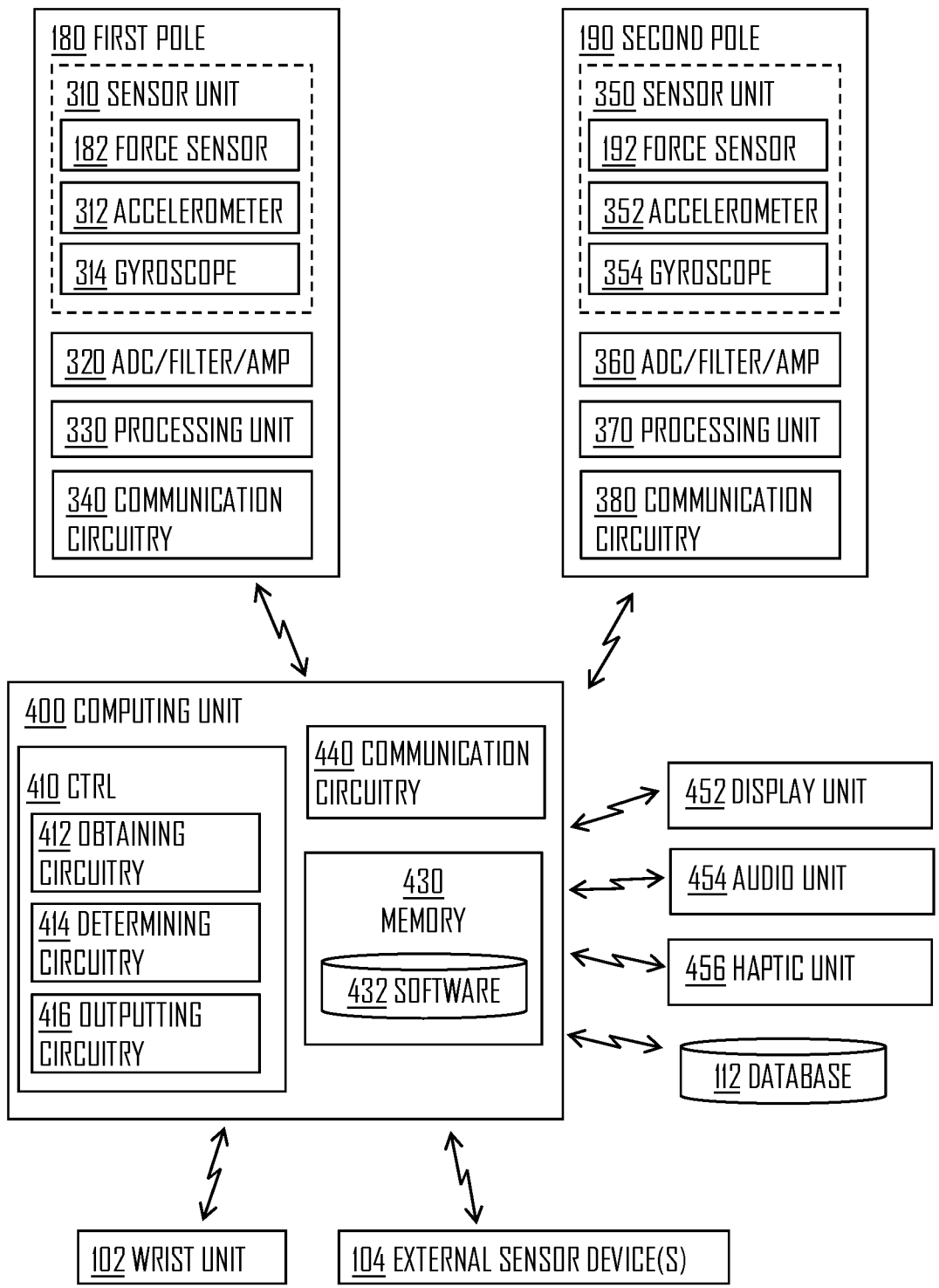
FIG. 3 illustrates a block diagram of the performance measuring system according to an embodiment.

FIG. 3 illustrates the system 100 according to an embodiment. Referring to FIG. 3, at least one pole 180, 190 and a computing unit 400 are illustrated. The computing unit 400 may be the computing unit performing the operations of block 210, 220, and 230. As described, the system 100 may comprise the computing unit 400 which may be configured to receive data from external or internal sensors to perform the operations of blocks 220 and 230, for example. In some embodiments, at least some of the sensors for providing force data and/or velocity data are comprised in the computing unit 400.

The pole 180, 190 (i.e. one or both of the poles 180, 190) may comprise a sensor unit 310, 350. The sensor unit 310, 350 may comprise the force sensor 182, 192. Additionally, the sensor unit 310, 350 may comprise an accelerometer 312, 352 and/or a gyroscope 314, 354. As described above, the sensor units 310, 350 may also comprise other sensors, such as cardiac activity sensor, barometer and/or satellite positioning circuitry.

In an embodiment, the pole 180, 190 comprises an analog-to-digital converter (ADC). In an embodiment, the pole 180, 190 comprises a filter. In an embodiment, the pole 180, 190 comprises an amplifier. The ADC, filter and/or the amplifier are indicated with block 320, 360. For example, the force sensor 182 may be configured to provide an electrical signal proportional to the induced force. The electrical signal may be amplified with the electrical amplifier and cover into digital form with the ADC. The digital signal may further be processed by a processing unit (e.g. microcontroller) to provide force readings in SI-unit (e.g. Newton). The processing unit may be a processing unit 330, 370 of the pole 180, 190 or a processing unit of the computing unit 400 (e.g. CTRL 410), for example.

The digital signal or the processed force reading (e.g. Newton) may be transmitted to the computing unit 400 by the pole 180, 190 via a communication circuitry 340, 380 of the pole 180, 190. Thus, the force data may comprise the raw measurement data in digital form and/or processed readings (e.g. Newton). Hence, the pole 180, 190 may be configured to provide raw measurement data or processed measurement data to the computing unit 400. In an embodiment, the system 100 comprises a wireless communication circuitry 340, 380 operatively coupled with the at least one force sensor 182, 192 and configured to wirelessly transmit force data. The force data may be transmitted to the computing unit 400, for example. In some embodiments, both poles comprises own wireless communication circuitry as shown in FIG. 2.

The processing unit 330, 370 may comprise at least one processor. Additionally, the processing unit 330, 370 may comprise at least one memory comprising computer program code (software). However, the processing unit 330, 370 may also be realized by ASIC(s).

The communication circuitry 340, 380 may comprise a wireless communication circuitry. Hence, one or both of the poles 180, 190 may be configured to transmit the force data (and possibly some other data, such as the velocity data) via air-interface to the computing unit 400. That is, the wireless communication circuitry may transform the force data (and possibly some other data) into electromagnetic energy that is transmitted via one or more antennas to the computing unit 400.

In an embodiment, the communication circuitry 340, 380 comprises a Bluetooth circuitry. The Bluetooth circuitry may enable data transfer and/or communication according to the Bluetooth specifications. For example, the communication circuitry may support Bluetooth Light Energy (BLE) (also referred to as Bluetooth Smart).

In some embodiments, the communication circuitry 340, 380 supports Near Field Communication (NFC) and/or similar induction based proximity communication technologies. In an embodiment, the communication circuitry 340, 380 supports induction based proximity communication. This may enable the pole(s) 180, 190 to be easily paired with each other and/or with the computing unit 400. For example, NFC may enable an easy way to sync time between different entities of the system.

In an embodiment, the communication circuitry 340, 380 supports ANT, ANT+, and/or ZigBee communications. Any suitable RF technique may be applied.

In an embodiment, the wireless communication circuitry 340, 380 comprises a Local Area Network (LAN) and/or wireless LAN (WLAN) circuitry (e.g. WiFi).

In order to receive data from the poles 180, 190, the computing unit 400 may comprise a communication circuitry 440. The communication circuitry 440 may support any of the communication protocols used by the communication circuitries 340, 380. Hence, data may be transferred from the poles 180, 190 to the computing unit 400 (e.g. sensor data) and from the computing unit 400 to the poles 180, 190 (e.g. sensor configuration data).

The communication between the computing unit 400 and the poles 180, 190 (or more precisely between the communication circuitries 340, 380, 440) may utilize a radio communication link (e.g. bidirectional or unidirectional radio links) or broadcasting, for example. That is, conventional radio link(s) according to the applied radio communication protocol may be used or the poles 180, 190 may be configured to broadcast sensor data to the computing unit 400 (e.g. Bluetooth broadcast).

However, in some embodiments, the computing unit 400 is comprised in the pole 180, 190. Hence, there may be no need to wirelessly transmit the sensor data, such as force or velocity data.

According to an embodiment with reference to FIG. 3, the computing unit 400 comprises the controller (CTRL) 410. The CTRL 410 may comprise at least one processor. Additionally, the computing unit 400 may comprise at least one memory 430 comprising the software 432 as described above. In an embodiment, the CTRL 410 comprises an obtaining circuitry 412 configured to obtain force data measured by at least one force sensor 182, 192 coupled with one or more skiing poles 180, 190 and velocity data measured by at least one sensor (e.g. accelerometer, satellite positioning circuitry) for measuring velocity of the user, a determining circuitry 414 configured to determine poling power based on the force data and the velocity data, and an outputting circuitry 416 configured to output a poling power indicator based on the determined poling power.

Let us now discuss the outputting step of block 230 in more detail. The outputting may comprise outputting a visual indication by a display unit 452, a, audio indication by an audio unit 454, and/or haptic indication by a haptic unit 456. The display unit 452, the audio unit 454, and/or the haptic unit 456 may be comprised in the computing unit 400, in the pole 180, in the pole 190, in the wrist unit, in the portable electronic device 106, and/or in the external sensor device(s) 104, for example. It is possible that an indication is outputted via one or more units using one or more indication types (e.g. visual, audio, haptic). For example, the pole or poles 180, 190 may comprise a display unit comprising one or more light emitters, such as Light Emitting Diodes (LEDs), for visually indicating the power indicator and the wrist unit 102 may comprise a display for displaying the power indicator.

For example, the display unit 452 may comprise one or more displays and one or more LEDs. For example, the audio unit 454 may comprise one or more speakers. For example, the haptic unit 456 may comprise one or more haptic elements (e.g. vibration element) configured to provide haptic feedback.

In case the display unit 452, the audio unit 454, and/or the haptic unit 456 are comprised in a device external to the computing device, the external device or the respective unit may comprise communication circuitry that enables control messages to be transmitted from the computing unit to the corresponding unit 452, 454, 456. Such communication circuitry may be configured to provide similar communication capabilities as the communication circuitry 340, 380. Thus, in an embodiment, the computing unit 400 is configured to transmit one or more control messages to the display unit 452, the audio unit 454, and/or the haptic unit 456. The control message(s) may cause the receiving unit to indicate the power indicator. The control messages may also relate to other metrics, such as cardiac activity, which are describe below in more detail.

According to an embodiment, the system 100 comprises at least one user interface for indicating the poling power indicator via visual indication, audio indication, and/or haptic indication. A user interface may comprise the display unit 452, the audio unit 454, and/or the haptic unit 456. In an embodiment, the system 100 comprises the wrist unit 102 configured to be worn by the user, wherein the wrist unit comprises a user interface unit for indicating the poling power indicator via at least one of visual indication, audio indication, and haptic indication. The wrist unit 102 may comprise a communication circuitry that may be similar to the communication circuitry 340, 380. This may enable the wrist unit to receive control message from the computing unit 400 in case where the computing unit is not situated at the wrist unit 102. However, in an embodiment, the computing unit 400 is comprised in the wrist unit 102.

In an embodiment, the pole 180 and/or pole 190 comprises a user interface element, such the display unit 452, the audio unit 454, and/or the haptic unit 456. It needs to be noted that a similar user interface element may be comprised in one or more elements of the system 100. For example, the user interface element may be configured to output one or more force and/or power indicators based on the force data and/or power data. For example, the pole 180, 190 may have one or more LEDs configured to output a certain color depending on the force data and/or power data. For example, if 300 N force or over is measured, the color may be red. For example, if 150-300 N force is measured, the color may be green. For example, if 150 N force or less is measured, the color may be blue. Thus, the user may immediately, on each push, determine whether the push force of each pole is suitable for the current situation. The pole 180, 190 may, in some embodiments, comprise a display. In an embodiment, the user interface is comprised in the grip part of the pole 180, 190.

In an embodiment, the elements 310, 320, 330, and/or 340 are comprised in a grip part of the pole 180. Said elements may be within the pole and/or grip such that they are protected against external forces. Similarly, elements of the pole 190 may be situated at the grip and/or within the grip.

In an embodiment, in addition to or as an alternative to the visual, audio, and/or haptic output, the outputting the poling power indicator comprises storing the poling power indicator in the database 112 of the system 100. For example, the poling power indicator may be recorded in to the database 112, or to a memory 430 from which it may be transferred to the database 112. The poling power indicator may be transferred to the server 114 from the computing unit 400, wherein the server 114 may be configured to store the power indicator to the database 112. It also needs to be noted that other kind of data and indicators may be stored to the database 112. For example, raw measurement data or processed measurement data (e.g. force data, velocity data, cardiac activity data, satellite positioning data, motion data) may be stored to the database 112. In an embodiment, the database 112 is external to the computing device 400. In an embodiment, the database 112 is comprised in a cloud network. In an embodiment, the database is comprised in the memory 430. So, in short, the outputting may comprise storing (i.e. inputting to another entity), the power indicator and/or some other indicator determined by the computing unit 400 based on measurement data provided by the sensor unit 310, 350, the wrist unit 102, and/or the external sensor device(s) 104 (i.e. comprising the sensor devices 104A, 104B, 104C).

FIG. 4A illustrates a skiing pole according to an embodiment. Referring to FIG. 4A, the pole, such as pole 180 or 190, is illustrated. The pole 180, 190 may comprise a handle or grip 480 and a pole part 486. The grip 480 and the pole may be joined together to from a skiing pole as it is known in the art. The pole may comprise the at least one force sensor 182. The at least one force sensor 182 may be situated at the grip 480. In particular, the force sensor 182 may be situated in the grip 480. According to an embodiment, the force sensor 182 comprises a load cell force sensor, such as an ElectroMechanical Film (EMFi) force sensor or a strain gauge. The force sensor 182 may be operatively connected to an adapter that enables the pole part 486 to be attached to the grip 480. In some embodiments, the force sensor 182 comprises a plurality of force sensors and sensor fusion circuitry. The sensor fusion circuitry may enable data from more than one force sensor to be selectively processed, for example. That is, data from multiple force sensors may be combined, for example.

In an embodiment, the at least one force sensor 182, 192 is configured to measure longitudinal forces applied to the at least one pole 180, 190. Longitudinal direction is shown in FIG. 4A with arrow F indicating the direction of the force F. F may denote the force in Newton. The longitudinal force may thus be understood to be parallel with the direction of the pole's 180, 190 elongating direction.

Figure 10A:
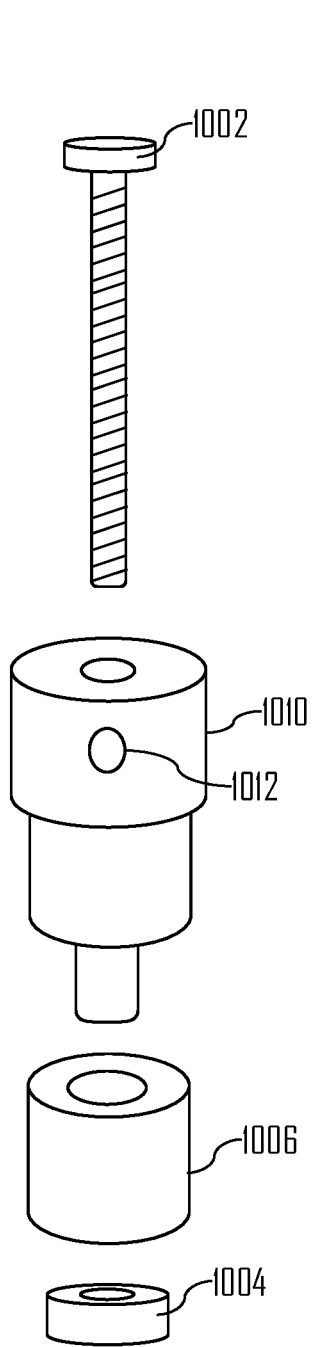
FIGS. 10A, 10B, 10C and 10D illustrate some embodiments.
Figure 10B:
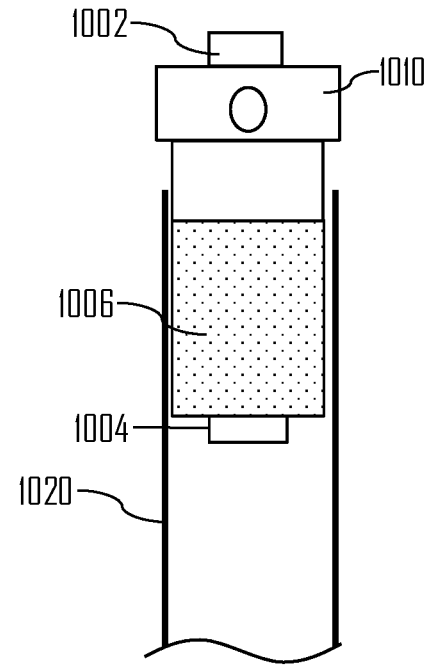
Figure 10C:
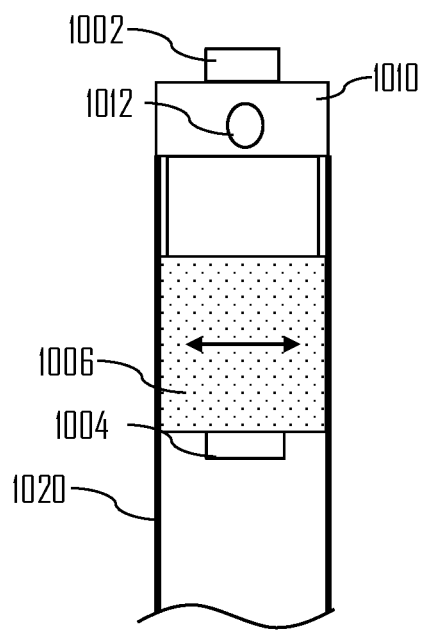
Figure 10D:
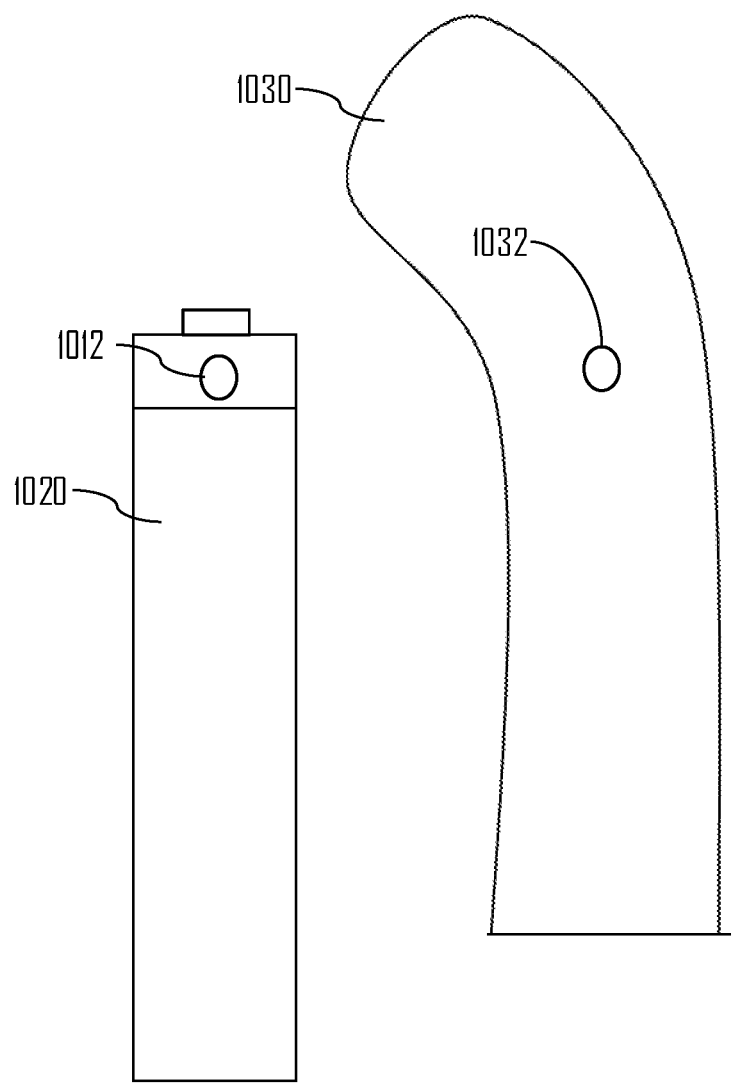

FIGS. 10A, 10B, 10C and 10D illustrate some embodiments. According to an example embodiment, FIG. 10A illustrates an adapter or socket for fixing and/or connecting a handle or grip to a pole part so as to form a pole. In FIG. 10D the pole part 1020 is shown to which the handle or grip 1030 may be attached using said adapter or socket. Hereinafter, the handle or grip 1030 is referred to as grip 1030 and said adapter or socket is referred to as adapter.

According to an example embodiment, the grip 1030 comprises the sensor unit 310, 350, element 320, 360, processing unit 330, 360 and/or communication circuitry 340, 380. In other words, the grip 1030 may comprise electronics of the pole described above and hereinafter. Hence, the grip 1030 may be a smart grip or smart handle configured to perform said force and/or power measurement. Accordingly, such grip 1030 may be attached to the pole par 1020 at the factory or by first removing original grip of the pole and replacing it with the smart grip 1030 to obtain a smart pole for measuring the poling power, for example.

Referring to FIG. 10A, the adapter may comprise an extension element 1006, such as a radially extending element. The extension element 1006 may be extended using fixing element(s) 1002, 1004, such as a nut 1004 and a bolt 1002. For example, the extension element 1006 may be placed between the nut 1004 and the bolt 1002, wherein the tightening the bolt 1002 and the nut 1004 with each other may pinch the extension element 1006 and thus extend it. For example, the extension element 1006 may be made of and/or comprise elastic or flexible material, such as rubber or silicone. Other parts of the adapter may comprise, for example, aluminum.

The adapter may further comprise the socket part 1010 comprising one or more fixing point 1012 (e.g. aperture and/or counterpart for screw or bolt). The fixing point(s) 1012 may be used to fix the grip 1030 to the adapter and thus to the pole part 1020. The grip 1030 may thus comprise corresponding fixing elements 1032 (e.g. aperture for the screw or bolt). Screws and/or bolts may thus be used to fix the grip 1030 to the pole part 1020 once the adapter is fixed to the pole part 1020. Example of this is shown in FIGS. 10B and 10C. That is, the pole part 1020 may be hollow such that the adapter may be arranged partially within the pole part 1020. Once the adapter is arranged within the pole part, the bolt 1002 and the nut 1004 may be tightened which may cause the extension element 1006 to radially extend (see arrow in FIG. 10C), thus fixing the adapter to the pole part 1020, i.e. inner surface of the pole part 1020. The fixing point 1012 may be visible such that the fixing the grip 1030 to the pole part 1020 may be enabled. This may be shown in FIGS. 10C and 10D. For example, the adapter and some of the pole part 1020 may be arranged within a hollow of the grip part 1030 such that the elements 1012 and 1032 are aligned with each other. Then the grip 1030 may fixed to the pole part 1020 using screw and bolts, for example.

Figure 5B:
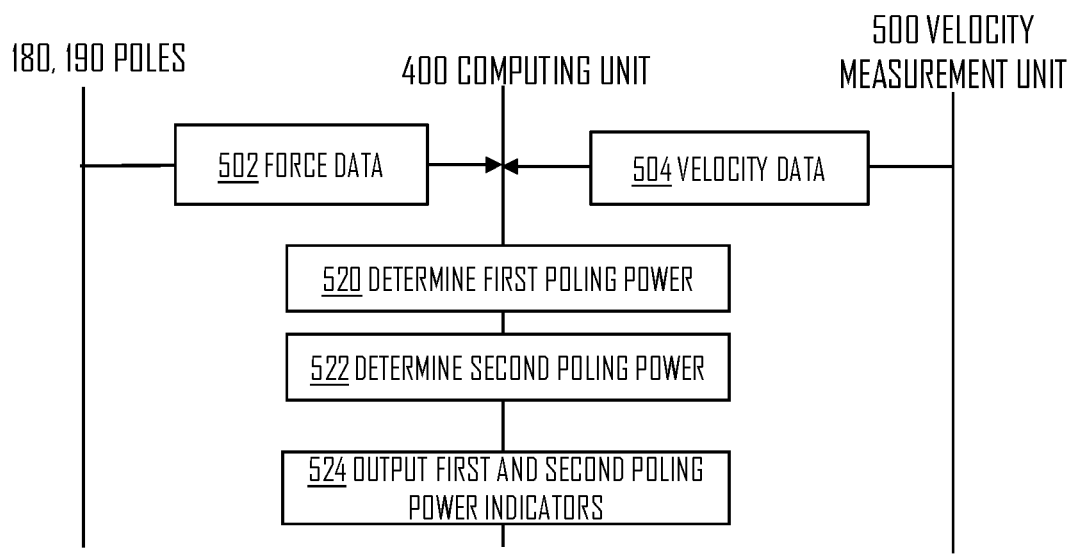

Let us then look closer on some embodiments with help of signal diagrams of FIGS. 5A, 5B, 6A, 6B, 7A, and 7B illustrating some embodiments. Referring to FIG. 5A, signaling between the pole(s) 180, 190, the computing unit 400 and a velocity measurement unit 500 may be shown. As described, in some embodiments all of these elements may be comprised in the same entity (E.g. in a pole), but in some embodiments they may be separate entities utilizing wireless communication therebetween. For example, the first pole 180 and/or the second pole 190 may measure and transmit force data to the computing unit 400 (block 502). The transmission may be wireless. The velocity measurement unit 500 may transmit velocity data to the computing unit (block 504). The transmission may be wireless. The velocity measurement unit 500 may denote the described at least one sensor for measuring velocity of the user 10. Hence, the velocity measurement unit 500 may be and/or comprise an accelerometer (e.g. 3D), a gyroscope (e.g. 3D), and/or satellite positioning circuitry (e.g. GPS, Glonass, Galileo). It is further yet again noted that the velocity measurement unit 500 may be shared between more than one entity. For example, the velocity data may be received from the pole(s) 180, 190, the wrist unit 102 and/or the external sensor device(s) 104. Further, force data and/or velocity data may be received from the sensor unit 310, 350 of the respective pole 180, 190 even though it is described as being received from the pole 180, 190.

In block 506, according to an embodiment, the computing unit 400 calculates or determines velocity based on the velocity data.

In block 508, according to an embodiment, the computing unit 400 calculates or determines force based on the force data.

In block 510, the computing unit 400 may determine the poling power. The poling power may be calculated as P=f(F, v), wherein P denotes the poling power, F denotes force, and v denotes velocity. Thus, P may be calculated as function of F and v.

The processes of blocks 506 and 508 may not mandatory. For example, the velocity data and the force data may already comprise explicit force and velocity values such that the poling power may be calculated. However, for example, if the velocity data comprises satellite positioning data and/or accelerometer and gyroscope data, the computing unit 400 may calculate the velocity for the block 510 based on the raw velocity data. For example, velocity data may simply comprise satellite positioning measurements received by an external satellite positioning circuitry. The velocity may be determined based on such measurements.

In block 512, the computing unit 400 may output the poling power indicator as described with various examples above. The poling power indicator may indicate the poling power at a certain time instant, during a certain time period, and/or indicate an average poling power during a certain time period, for example. The poling power indicator may indicate poling power in Watts (W), for example. The indicated poling power may be a current poling power or poling power at certain time instant, for example. For example, the indicated poling power may be an average poling power during a certain measurement time period. In some embodiments, the poling power indicator indicates both the average poling power and current poling power (or the poling power at certain time instant). Also, the power indicator may be pole-specific. That is, there may be a power indicator for each pole in the system. However, the power indicator may be common to the poles of the system. Also, there may be pole-specific power indicator and common power indicators.

FIG. 5B illustrates an embodiment. Referring to FIG. 5B, in blocks 502, 504 the computing unit 400 may receive the force and velocity data. In this case, the computing unit 400 receives force data from both poles 180, 190. Thus, the computing unit 400 may receive first force data associated with the first pole 180 and second force data associated with the second pole 190.

In block 520, the computing unit 400 may determine first poling power associated with the first skiing pole 180 (i.e. based on the first force data and the velocity data). In block 522, the computing unit 400 may determine second poling power associated with the second skiing pole 190 (i.e. based on the second force data and the velocity data). Additionally or alternatively, a third poling power indicating poling power of both poles 180, 190 may be calculated based on the first and second force data and the velocity data.

In block 524, the computing unit 400 may output a first poling power indicator based on the first poling power and a second poling power indicator based on the second poling power. Additionally or alternatively, a third poling power indicator based on the third poling power may be outputted. The third poling power indicator may, for example, indicate average poling power of the first and second poles 180, 190.

Figure 6A:
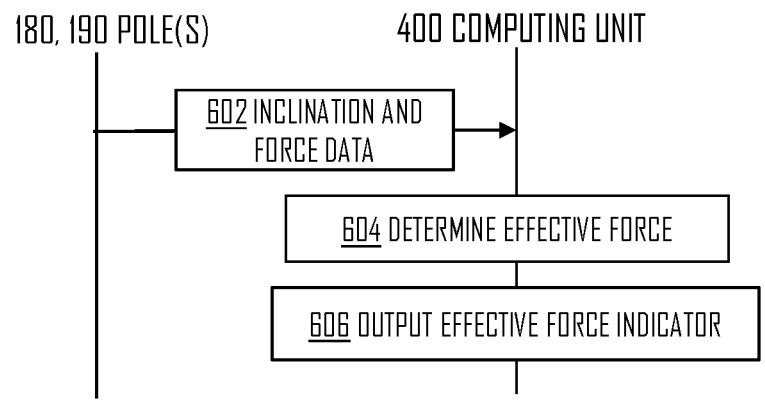

FIG. 6A illustrates an embodiment related to measuring inclination data about the one or more skiing poles 180, 190. Referring to FIG. 6A, in block 602, the computing unit may obtain inclination data associated with the one or more poles 180, 190. For example, the sensor unit 310, 350, and more particularly, the accelerometer 312, 352 and the gyroscope 314, 354 may provide such inclination data. FIG. 4B shows what is meant by inclination. Referring to FIG. 4B, the inclination data may indicate angle A between the pole 180 and a plane on which the user skis or walks. As shown measured force (e.g. longitudinal force) F may be divided into components including Fx and Fy. Additionally, there may be third component not shown in FIG. 4B. Hence, the force may be determined three dimensionally (i.e. 3D).

With reference to FIG. 6A, in block 604, the computing unit 400 may determine, based at least on the force data and the inclination data received from the pole(s) 180, 190, magnitude of a horizontal force component Fx. In block 606, the computing unit 400 may output at least one indicator based at least partly on said magnitude of the horizontal force component. For example, the power indicator calculated in block 220 and outputted in block 230 may be calculated based on the velocity data and the horizontal force component. However, calculating and outputting the power indicator may not be necessary. Instead or additionally, the computing unit may output an effective force indicator indicating the horizontal force component or components. Outputting the effective force indicator (also referred to as horizontal force indicator or simply force indicator) may mean at least one of displaying the effective force indicator, audibly outputting the effective force indicator, outputting a haptic feedback indicating the effective force indicator, and storing the effective force indicator in a memory, such as the database 112. Outputting the force indicator may be similar to the outputting the power indicator.

According to an aspect, the computing unit is configured to determine the horizontal force component independently from the poling power determination. Hence, determining poling power may not be needed when determining the horizontal force component. In some embodiments, the horizontal force component Fx is referred to as effective force as it is the force that causes a supporting counterforce −Fx (being opposite to Fx) that pushes the user 10 forward according to laws of physics. Basically, in the power calculation any of Fx and −Fx may be used as long as absolute value of the used force value is used.

According to an embodiment, the horizontal force component is substantially parallel with a movement direction 492 of the user 10. This can be seen in FIG. 4B. Parallel may comprise −Fx and Fx forces (i.e. to same direction or to opposite direction compared with the direction 492).

Referring to FIG. 4C, another dimension, compared with FIG. 4B, may be shown, wherein −Fx may not be parallel with the movement direction 492. However, −Fx may still be a horizontal force although not to the exact same direction as arrow 492 (e.g. to left or right compared with movement direction 492). For example, if the force is determined using only two dimensional measurement, the determined horizontal force may not be exactly parallel with the movement direction. However, this accuracy may be sufficient for many applications. Actually, for example, during skating skiing, the skier may move locally from left to right and right to left compared with the overall movement direction. Hence, it may be beneficial to measure effective forces that have an effect to the local and overall movement of the skier.

The inclination data, and hence the horizontal or effective force, may be determined based on measurements by the accelerometer and gyroscope of the sensor unit of the respective pole. Additionally, magnetometer may be used to detect the inclination data. The movement direction 492 may be determined using satellite positioning data, accelerometer data, magnetometer, and/or gyroscope data. The data for the movement direction determination may be acquired from the pole 180, 190 and/or from some other device, such as the wrist unit 102 and/or the external sensor device(s) 104, to name a couple of examples.

Figure 6B:
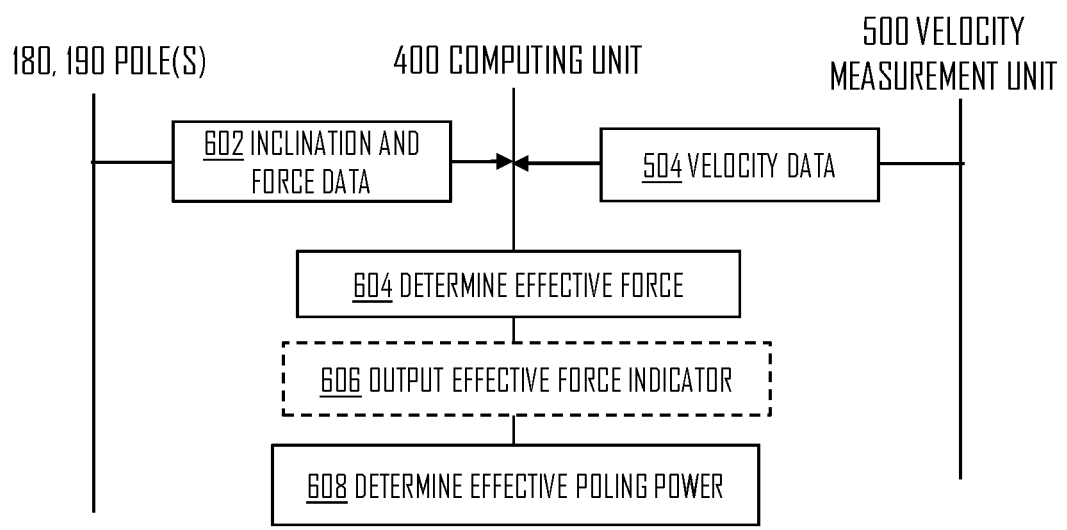

FIG. 6B illustrates yet another embodiment. Referring to FIG. 6B, the computing unit 400 may receive velocity data indicating velocity of the user (block 504) from the unit 500. In block 602, the computing unit 400 may receive inclination data and force data from the pole or poles 180, 190. In block 604, the effective force may be determined as described above in connection with FIG. 6A. However, block 606 may not be necessary. Hence, it may be performed. However, in block 608, the computing unit may determine effective poling power based on the effective force. That is, the poling power determined, for example, in block 220 may be determined based on said magnitude of the horizontal force component and the velocity data. Accordingly, the determined poling power may be outputted.

Figure 7A:
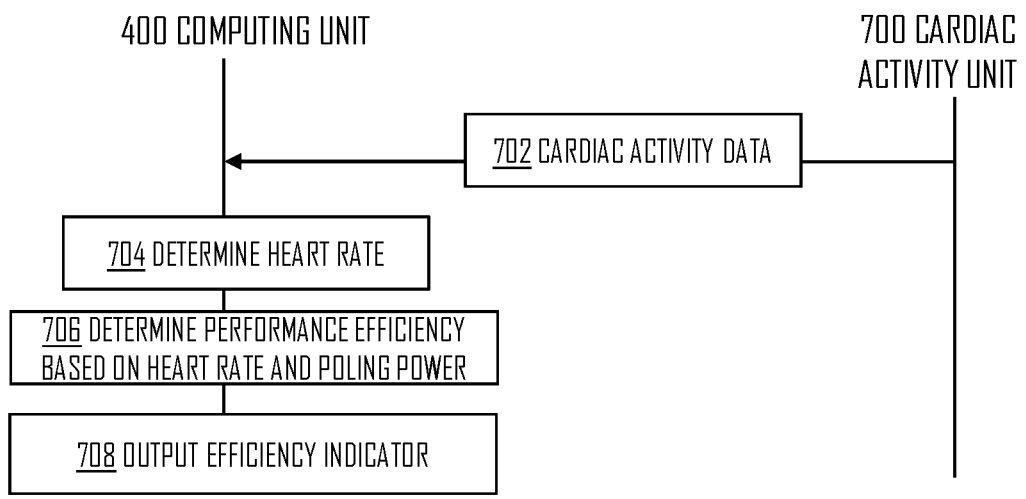
Figure 7B:
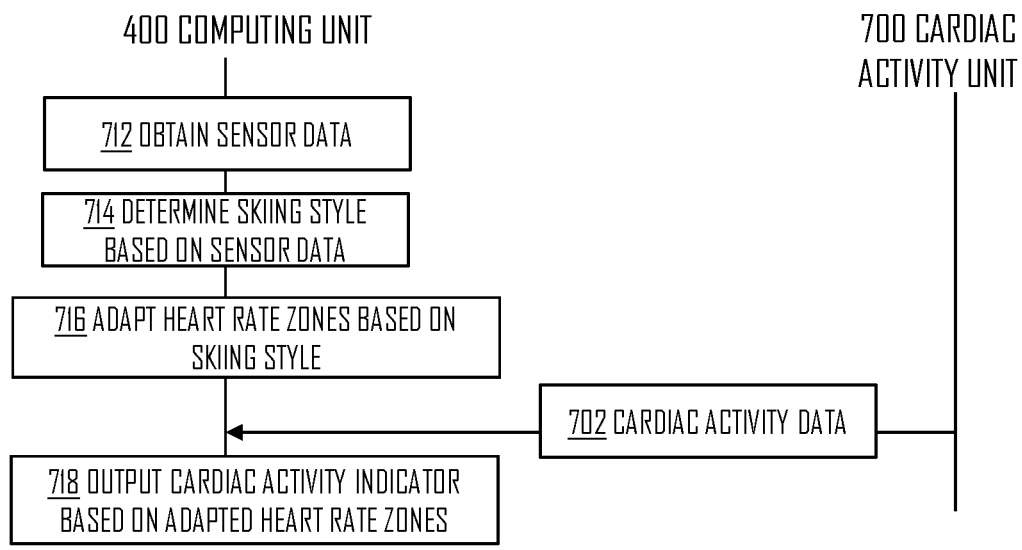

Let us then look closer on FIGS. 7A to 7B showing some embodiments regarding cardiac activity measurement that may bring further benefits for the performance monitoring of the system utilizing poles. Referring to FIG. 7A, the system may further obtain cardiac activity data of the user measured by at least one cardiac activity sensor (block 702). As discussed, the system may comprise one or more cardiac activity sensors utilizing one or more technologies. For example, wrist unit 102 enabling optical cardiac activity measurement may be used to obtain the data. Hence, if the computing unit 400 is comprised in the wrist unit 102, there may be no need to transmit said data. However, if a cardiac activity sensor external to the computing unit 400 is used, the transmission (e.g. wireless transmission) may be required. Said transmission may utilize Bluetooth, WLAN and/or cellular communication, for example. The at least one cardiac activity sensor is visualized as a cardiac activity unit 700 in FIGS. 7A to 7B. As already discussed, the cardiac activity unit 700 may provide cardiac activity data (e.g. heart rate data, HRV data and/or HBI data) to the computing unit 400. The cardiac activity unit 700 may thus comprise, for example, one or more sensors, such as optical cardiac activity sensor, bioimpedance sensor, and/or electrodes.

In an embodiment, the computing unit causes outputting of at least one indicator based at least partly on the cardiac activity data. In an embodiment, the outputting comprises outputting a cardiac activity indicator based on the cardiac activity data. For example, such indicator(s) may include heart rate indicator, HRV indicator, HBI indicator, and/or heart rate zone indicator, to name a few examples.

According to an embodiment, in block 704, the system (e.g. the computing unit 400) may determine heart rate of the user based on the cardiac activity data. In block 706, the computing unit 400 may determine performance efficiency based on the determined poling power (e.g. block 220) and the determined heart rate. In block 708, an efficiency indicator indicating the determined performance efficiency may be outputted.

The performance efficiency may denote skiing efficiency, for example. However, performance efficiency of, for example, nordic walking may similarly be determined using the described method. The efficiency indicator may be calculated by comparing the poling power to the determined heart rate. Higher poling power and lower heart rate may indicate high performance. As the poling power decreases and/or heart rate increases, the performance efficiency may also decrease. For example, the performance efficiency indicator may be calculated for a certain training session and be indicated using a numeric value. Thus, comparing the performance efficiency indicator between training sessions may be useful to the user. In a way, it may be understood that the performance efficiency indicator indicates how much poling power is produced with a certain heart rate. In some embodiment, the performance efficiency indicator calculation takes further input parameters, such as skiing style (explained below with reference to FIG. 7B), velocity data, and poling angle (e.g. inclination data). For example, it is noted that skating and classic styles of skiing may induce different heart rates. Hence, in an embodiment, the performance efficiency indicator is specific to the type of physical exercise (e.g. skiing, nordic walking) and/or style of physical exercise (e.g. skating, classic).

Referring to FIG. 7B, in block 712, the computing unit 400 may obtain sensor data from one or more sensors. This sensor data may be used, in block 714, to determine type of physical exercise and/or skiing style (i.e. in case the physical exercise is skiing). For example, one or more algorithms using motion data may be used to determine pole movement pattern from which the type of activity may be determine from. For example, classic style skiing and skating style skiing may be associated with distinct movement patterns and/or motion data measured from the poles or from the legs of the user using one or more leg sensors. Additionally or alternatively, the type of physical exercise and/or skiing style may be determined based on user input. For example, the user may select classic style skiing measurement to be initiated on his/her wrist unit 102. Thus, the computing unit 400 may determine that the physical exercise is classic skiing.

The sensor data obtained in block 712 may comprise the force data, the velocity data, and/or motion data measured using at least one motion sensor. The velocity data and motion data may in some instances mean the same thing. That is, velocity data may comprise measurement data by one or more motion sensors (e.g. accelerometer, gyroscope, and magnetometer). In an embodiment, the system 100 comprises a motion circuitry configured to measure physical motion data of the user. The motion circuitry may be comprise in the computing unit 400, in the poles 180, 190 and/or in the external sensor device(s) 104. The motion circuitry may be shared between said entities in some embodiments. Physical motion data may comprise velocity data, acceleration data, direction data, orientation data, and/or position data, for example. The motion circuitry may comprise one or more accelerometers, one or more gyroscopes, and/or one or more satellite positioning circuitries (e.g. GPS and/or GLONASS circuitries). In some embodiments, the motion circuitry (also referred to as motion sensing circuitry) comprises one or more magnetometers for measuring the direction and/or orientation data.

In an embodiment, the motion circuitry comprises an accelerometer and a gyroscope. The motion circuitry may further comprise sensor fusion software for combining the accelerometer data and gyroscope data so as to provide physical quantities, such as acceleration data, velocity data, or limb trajectory data in a reference coordinate system having orientation defined by a predetermined gyroscope orientation.

In an embodiment, the motion circuitry comprises a gyroscope and a magnetometer. The motion circuitry may further comprise sensor fusion software to combine gyroscope data and magnetometer data so as to provide a reference coordinate system for the gyroscope based on the Earth magnetic field measured by the magnetometer. In general, the sensor fusion software described above may combine measurement data acquired from at least two motion sensors such that measurement data acquired from one motion sensor is used to establish the reference coordinate system for the measurement data acquired from at least one other motion sensor. Thus for example, the satellite positioning data may also be utilized in the sensor fusion.

In an embodiment, the motion circuitry comprises a sensor fusion circuitry configured to combine data from two or more sensors. The two or more sensors may be comprised in the motion circuitry it and/or in some external device(s) (e.g. external sensor device(s) 104). For example, the motion circuitry may be configured to combine data from one or more accelerometers, one or more gyroscopes, and/or one or more satellite positioning circuitries.

Referring again to FIG. 7B, the computing unit 400 may adapt heart rate zones of the user based on the determine type of physical exercise and/or style of skiing (block 716). Thus, in block 718, the computing unit 400 may output a cardiac activity indicator based on the adapted heart rate zones and the obtained cardiac activity data (obtained in block 702). For example, the computing unit may output a heart rate zone indicator. For example, the heart rate zone indicator may indicate the current heart rate zone or heart rate zone as a function of time. Heart rate zones may each indicate a certain heart rate zone having a lower and upper limits. Heart rate zones may further be based on personal characteristics of the user (e.g. age, gender, weight, and/or height). These parameters may be obtained by the computing unit as a user input, for example. It further needs to be noted that the sequence of steps listed in FIG. 7B may not be necessary. That is, for example, the cardiac activity data (block 702) may be acquired before the blocks 712-716.

Figure 8A:
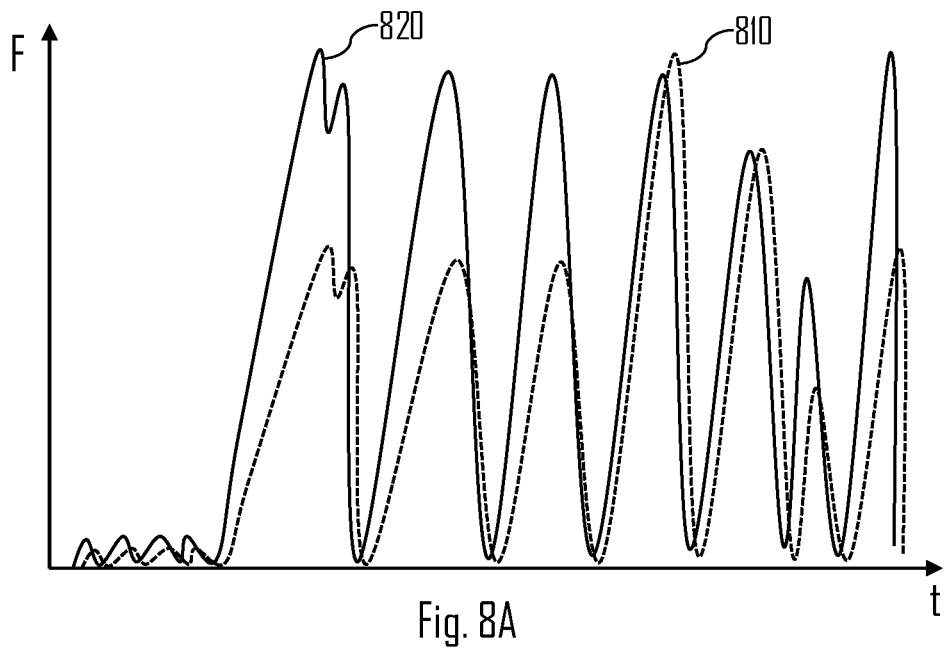
FIGS. 8A and 8B illustrate some embodiments.
Figure 8B:
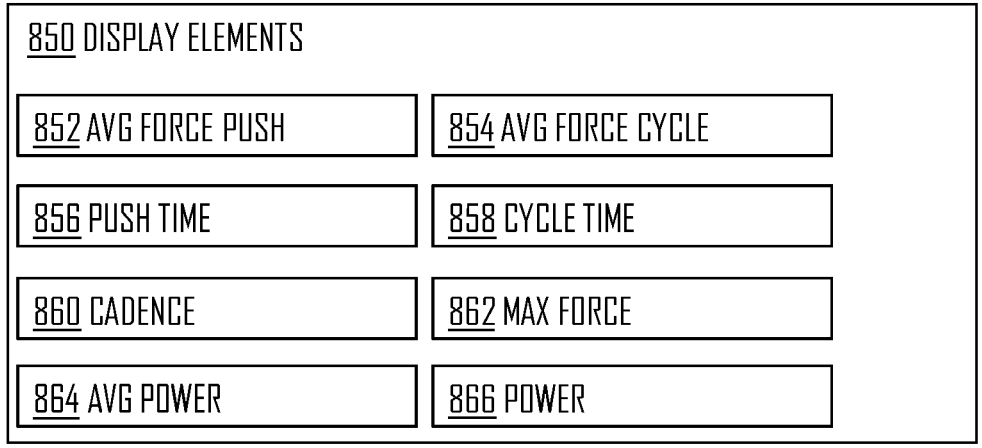

FIGS. 8A to 8B illustrate some further embodiments. Referring to FIG. 8A, poling force may be indicated as a function of time. From the poling force (i.e. indicated as force data), poling power may be determine as described above with the help of velocity data. In FIG. 8A, poling force of the first pole 180 is indicated with dotted line 810 and poling force of the second pole 190 is indicated with solid line 820. As it can be observed, the poling force of different poles may differ. Thus, the poling power between poles may differ. This may be valuable information for a user, for example, if he/she wants to improve his muscle balance or technique.

Referring to FIG. 8B, some display options by the display unit 452 are illustrated. Not all display options are indicated. However, the display elements 850 that may be displayed by the display unit 452 may comprise average force push 852, average force cycle 854, push time 856, cycle time 858, cadence 860, max force 862, average power 864, and/or power 866. Further, the display elements 850 may comprise cardiac activity indicator (e.g. heart rate zone indicator) and/or efficiency indicator (e.g. skiing efficiency indicator), for example. Each of the display elements 852-866 may indicate the corresponding value for one or more poles. Average value may mean an average value for a certain time period (e.g. for certain training session).

According to an embodiment, the system 100 is configured to measure the poling power and output the poling power indicator during the physical activity (e.g. skiing) performed by the user. Hence, the pole 180 and/or the pole 190 may be in real-time communication with the computing unit 400 (e.g. the wrist unit 102). Real-time communication may mean, for example, that the pole 180, 190 is paired with the computing unit during the physical exercise, i.e. communicatively coupled.

Figure 9:
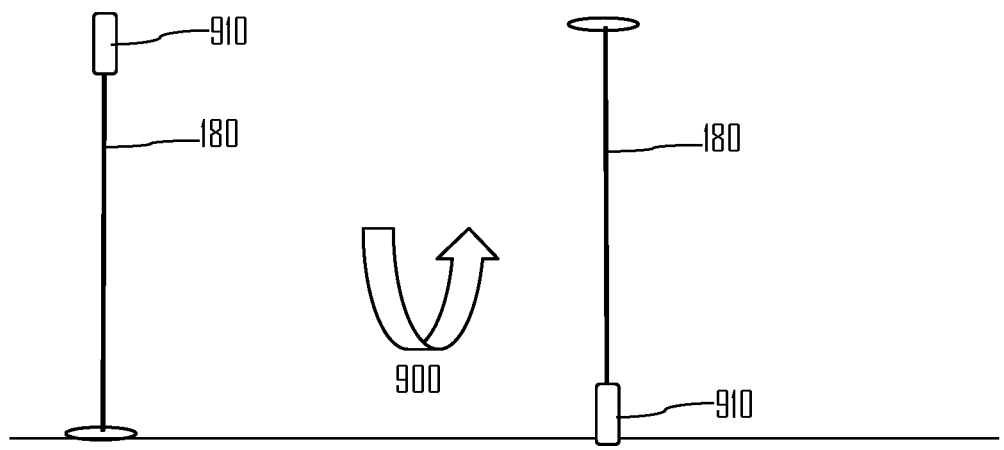
FIG. 9 illustrates a weather station pole according to an embodiment.

FIG. 9 illustrate yet another embodiment. Referring to FIG. 9, the pole 180 is used as an example, but the described solutions and functionalities may be applicable to any pole described above (e.g. pole 190). The pole 180 may comprise one or more environmental sensors 910. The environmental sensor(s) 910 may comprised in the sensor unit 310, for example, and configured to measure one or more environmental values. The environmental data measured by the environmental sensor(s) 910 may be outputted similarly as, for example the power indicator using a user interface or memory of the pole 180 and/or some external entity (e.g. wrist unit 102). The environmental sensor(s) 910 may comprise temperature sensor(s), humidity sensor(s) and/or barometer(s). Thus, the environmental data may comprise temperature data, humidity data and/or air pressure data. The environmental data may be, for example, transmitted to the wrist unit 102 for display and/or stored to the database 112.

The environmental sensor(s) 910 (also referred to as an environmental sensing unit) may be configured to measure both air and snow related values. E.g. snow temperature and air temperature; snow humidity and air humidity. In an embodiment, the environmental unit comprises a switch (may be a part of the processing unit functionality or a separate switch) that automatically configures the measurement according flip of the pole 180 (shown with arrow 900. I.e. in FIG. 9, the pole 180 may first be in normal use position (i.e. upright position) meaning that the environmental sensors 910 are in connection with air. However, the pole 180 is flipped around to upside-down position, the environmental sensors 910 may be placed in the snow. Thus, snow related values may be measured. Hence, in an embodiment, the environmental sensing unit 910 changes sensor configuration based on accelerometer data (e.g. using 3D accelerometer(s)) from the sensor unit 310. The configuration may be changed between the air sensing and snow sensing or ground sensing. More particularly, the processing unit 330 or the environmental sensing unit 910 obtains accelerometer data, and determines based on said data whether the pole 180 is in a first position (i.e. upright position) or in a second position (i.e. upside-down position). To be even clearer, the first position may mean that the grip of the pole 180 is above basket and/or point of the pole 180 (i.e. point is towards ground), and the second position may mean that the grip of the pole 180 is below the basket and/or point of the pole 180 (i.e. point is towards sky). Thus, the pole 180 may be configured to act as a weather station pole.

In an embodiment, the computing unit is configured to output at least one of air temperature, air pressure, air humidity, snow temperature, and snow humidity. Outputting may be similar as outputting the power indicator. For example, different environmental parameters may be showed together with a route recorded using satellite positioning circuitry. Further, power indicator(s), force indicator(s), cardiac activity indicator(s) and/or efficiency indicator(s) may be showed together with the environmental parameters and route. In an embodiment, the environmental parameters (i.e. comprising air temperature, air pressure, air humidity, snow temperature, and/or snow humidity) are used as input data for determining the efficiency indicator. That is, for example, colder snow may increase friction and thus have an effect on the performance efficiency.

It further needs to be noted that, according to an embodiment, the described system supports time syncing. That is, the different computational entities situated at different physical entities may be in sync with each other. For example, the first pole 180 and the second pole 190 may be in sync. This may mean that the data measured by the force sensor 182 and the force sensor 192 may be processed and monitored as simultaneous measurements. However, the skilled person will know what is meant by time synced system. The syncing between different entities may be based on radio communication (e.g. using communication circuitries). That is, radio signal(s) may be transmitted between different entities, wherein the radio signal(s) may carry data or information for syncing clocks at different entities. Another example may be the use of satellite positioning circuitry or circuitries, such as GPS, GLONASS and/or Galileo. That is, received satellite signal may indicate current time which may be then used to sync the clock at the receiving entity. It may also be possible to use both methods: i.e. one entity (e.g. the computing unit 400) may receive satellite signal which enables it to sync its time. Furthermore, said one entity may transmit a timing or syncing signal to other entities (e.g. the first pole, second pole) of the system, wherein the timing or syncing signal is based on the received satellite signal and causes the receiving entities to sync their clocks. Hence, time within the system may be synchronized. Similarly, measurements by other entities of the system may be synced. For example, the cardiac activity unit 700 may be synced with the pole(s) 180, 190 and/or with the computing unit 400. Hence, force data, velocity data, and cardiac activity data may be processed and monitored such that the entities providing said data are in sync with each other. This enables the force data, velocity data, and cardiac activity to be more comparable with each other, e.g. different performance metrics may be calculated more accurately.

As used in this application, the term 'circuitry' refers to all of the following: (a) hardware-only circuit implementations, such as implementations in only analog and/or digital circuitry, and (b) combinations of circuits and software (and/or firmware), such as (as applicable): (i) a combination of processor(s) or (ii) portions of processor(s)/software including digital signal processor(s), software, and memory(ies) that work together to cause an apparatus to perform various functions, and (c) circuits, such as a microprocessor(s) or a portion of a microprocessor(s), that require software or firmware for operation, even if the software or firmware is not physically present. This definition of 'circuitry' applies to all uses of this term in this application. As a further example, as used in this application, the term 'circuitry' would also cover an implementation of merely a processor (or multiple processors) or a portion of a processor and its (or their) accompanying software and/or firmware.

In an embodiment, at least some of the processes described above (e.g. in connection with FIGS. 1 to 10D) may be carried out by an apparatus comprising corresponding means for carrying out at least some of the described processes. Some example means for carrying out the processes may include at least one of the following: detector, processor (including dual-core and multiple-core processors), digital signal processor, controller, receiver, transmitter, encoder, decoder, memory, RAM, ROM, software, firmware, display, user interface, display circuitry, user interface circuitry, user interface software, display software, circuit, antenna, antenna circuitry, and circuitry. In an embodiment, the at least one processor, the memory, and the computer program code form processing means or comprises one or more computer program code portions for carrying out one or more operations according to any one of the embodiments described above (e.g. in connection to FIGS. 1 to 10D) or operations thereof.

According to yet another embodiment, the apparatus carrying out the embodiments comprises a circuitry including at least one processor and at least one memory including computer program code. When activated, the circuitry causes the apparatus to perform at least some of the functionalities according to any one of the embodiments described above (e.g. in connection with FIGS. 1 to 10D), or operations thereof.

The techniques and methods described herein may be implemented by various means. For example, these techniques may be implemented in hardware (one or more devices), firmware (one or more devices), software (one or more modules), or combinations thereof. For a hardware implementation, the apparatus(es) of embodiments may be implemented within one or more application-specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described herein, or a combination thereof. For firmware or software, the implementation can be carried out through modules of at least one chip set (e.g. procedures, functions, and so on) that perform the functions described herein. The software codes may be stored in a memory unit and executed by processors. The memory unit may be implemented within the processor or externally to the processor. In the latter case, it can be communicatively coupled to the processor via various means, as is known in the art. Additionally, the components of the systems described herein may be rearranged and/or complemented by additional components in order to facilitate the achievements of the various aspects, etc., described with regard thereto, and they are not limited to the precise configurations set forth in the given figures, as will be appreciated by one skilled in the art.

Embodiments as described may also be carried out in the form of a computer process defined by a computer program or portions thereof. Embodiments of the methods described above (e.g. in connection with FIGS. 1 to 10D) may be carried out by executing at least one portion of a computer program comprising corresponding instructions. The computer program may be in source code form, object code form, or in some intermediate form, and it may be stored in some sort of carrier, which may be any entity or device capable of carrying the program. For example, the computer program may be stored on a computer program distribution medium readable by a computer or a processor. The computer program medium may be, for example but not limited to, a record medium, computer memory, read-only memory, electrical carrier signal, telecommunications signal, and software distribution package, for example. The computer program medium may be a non-transitory medium, for example. Coding of software for carrying out the embodiments as shown and described is well within the scope of a person of ordinary skill in the art. In an embodiment, a computer-readable medium comprises said computer program.

Even though the invention has been described above with reference to an example according to the accompanying drawings, it is clear that the invention is not restricted thereto but can be modified in several ways within the scope of the appended claims. Therefore, all words and expressions should be interpreted broadly and they are intended to illustrate, not to restrict, the embodiment. It will be obvious to a person skilled in the art that, as technology advances, the inventive concept can be implemented in various ways. Further, it is clear to a person skilled in the art that the described embodiments may, but are not required to, be combined with other embodiments in various ways.

The invention claimed is:

1. A system for monitoring performance of a user, the system comprising:
at least one processor; and
at least one memory including a computer program code, wherein the at least one memory and the computer program code are configured, with the at least one processor, to cause the system to perform operations comprising:
obtaining force data measured by at least one force sensor coupled with one or more poles and velocity data measured by at least one sensor for measuring velocity of the user;
determining poling power based on the force data and the velocity data; and
outputting a poling power indicator based on the determined poling power, wherein the system further comprises:
at least one grip comprising the at least one force sensor; and
at least one adapter configured to enable the at least one grip to be attached to at least one pole, wherein the at least one adapter comprises a flexible extension element configured to radially extend to enable attachment of the at least one adapter to the at least one pole, wherein the flexible extension element is configured to radially extend inside a hollow of the pole using one or more fixing elements.

2. The system of claim 1, wherein the at least one force sensor comprises a first force sensor coupled with a first pole and a second force sensor coupled with a second pole.

3. The system of claim 2, wherein the at least one memory and the computer program code are configured, with the at least one processor, to cause the system further to perform operations comprising:
determining first poling power associated with the first pole based on force data from the first force sensor and the velocity data; and
determining second poling power associated with the second pole based on force data from the second force sensor and the velocity data,
wherein outputting the poling power indicator comprises outputting a first poling power indicator based on the first poling power and a second poling power indicator based on the second poling power.

4. The system of claim 1, wherein the at least one memory and the computer program code are configured, with the at least one processor, to cause the system further to perform operations comprising:
obtaining inclination data associated with the one or more poles;
determining, based at least on the force data and the inclination data, magnitude of a horizontal force component; and
outputting at least one indicator based at least partly on said magnitude of the horizontal force component.

5. The system of claim 4, wherein the horizontal force component is substantially parallel with a movement direction of the user.

6. The system of claim 4, wherein the at least one memory and the computer program code are configured, with the at least one processor, to cause the system further to perform operations comprising determining the poling power based on said magnitude of the horizontal force component and the velocity data.

7. The system of claim 1, wherein the at least one memory and the computer program code are configured, with the at least one processor, to cause the system further to perform operations comprising:
obtaining cardiac activity data of the user measured by at least one cardiac activity sensor; and
outputting at least one indicator based at least partly on the cardiac activity data.

8. The system of claim 1, wherein the at least one memory and the computer program code are configured, with the at least one processor, to cause the system further to perform operations comprising:
determining, based on at least one of the force data, the velocity data, motion data measured using at least one motion sensor, and user input, a type of physical activity performed by the user using the one or more poles; and
adapting heart rate zones of the user based on the determined type of physical activity.

9. The system of claim 8, wherein the at least one memory and the computer program code are configured, with the at least one processor, to cause the system further to perform operations comprising:
obtaining cardiac activity data of the user measured by at least one cardiac activity-sensor; and
outputting a cardiac activity indicator based on the cardiac activity data and the adapted heart rate zones.

10. The system of claim 7, wherein the at least one memory and the computer program code are configured, with the at least one processor, to cause the system further to perform operations comprising:
determining heart rate of the user based on the cardiac activity data;
determining performance efficiency of the user based on the determined poling power and the determined heart rate; and
outputting an efficiency indicator based on the determined performance efficiency.

11. The system of claim 1, wherein the at least one force sensor is configured to measure longitudinal forces applied to the one or more poles.

12. The system of claim 1, further comprising a wireless communication circuitry operatively coupled with the at least one force sensor and configured to wirelessly transmit force data.

13. The system of claim 1, further comprising at least one user interface unit for indicating the poling power indicator via at least one of visual indication, audio indication, and haptic indication.

14. The system of claim 13, further comprising a wrist unit configured to be worn by the user, wherein the wrist unit comprises the user interface unit for indicating the poling power indicator via at least one of the visual indication, the audio indication, and the haptic indication.

15. The system of claim 1, wherein the outputting the poling power indicator comprises storing the poling power indicator in a database of the system.

16. The system of claim 1, wherein the one or more fixing elements comprise a nut and a bolt, and the flexible extension element is placed between the nut and the bolt, wherein tightening of the bolt and the nut with each other pinches the flexible extension element and thus radially extends the flexible extension element inside the hollow of the pole.

17. The system of claim 1, wherein the at least one adapter comprises a socket part comprising one or more fixing points, and the at least one grip comprises corresponding fixing elements with which the at least one grip is fixed to the at least one adapter and thus to the one or more poles.

18. The system of claim 1, wherein the one or more grip comprises a hollow to receive the at least one adapter attached to the at least one pole.

\* \* \* \* \*